US006070127A

United States Patent [19]
Hirono et al.

[11] Patent Number: 6,070,127
[45] Date of Patent: May 30, 2000

[54] METHOD OF SUPERPOSING MOLECULAR CONFORMATIONS OF COMPOUNDS

[75] Inventors: Shuichi Hirono, Akatsukashin-machi; Kazuhiko Iwase, Showa-machi, both of Japan

[73] Assignee: Kyorin Pharmaceutical Co., Ltd., Tokyo, Japan

[21] Appl. No.: 08/957,072

[22] Filed: Oct. 24, 1997

[30] Foreign Application Priority Data

Apr. 25, 1997 [JP] Japan ..................................... 9-123425

[51] Int. Cl.[7] ..................................................... G01N 31/00
[52] U.S. Cl. ............................... 702/27; 702/22; 702/30; 395/500.33
[58] Field of Search ................................ 702/27, 22, 30; 395/500.33

[56] References Cited

PUBLICATIONS

Y.C. Martin, et al., Journal of Computer–Aided Molecular Design, vol. 7, pps. 83–102, "A Fast New Approach to Pharmacophore Mapping and its Application to Dopaminergic and Benzodiazepine Agonists", 1993.

R. Carbó, et al., International Journal of Quantum Chemistry, vol. 17, pps. 1185–1189, "How Similar is a Molecule to Another? An Electron Density Measure of Similarity Between Two Molecular Structures", 1980.

W.G. Richards, et al., Chemistry in Britain, vol. 24, pps. 1141, 1143, and 1144, "Molecular Similarity", Nov., 1988.

E.E. Hodgkin, et al., International Journal of Quantum Chemistry, Quantum Biology Symposium 14, pps. 105–110, "Molecular Similarity Based on Electrostatic Potential and Electric Field", 1987.

C. Burt, et al., Journal of Computational Chemistry, vol. 11, No. 10, pps. 1139–1146, "The Application of Molecular Similarity Calculations", 1990.

T.D.J. Perkins, et al., Journal of Computer–Aided Molecular Design, vol. 9, pps. 479–490, "Molecular Surface–Volume and Property Matching to Superpose Flexible Dissimiliar Molecules", 1995.

R. Carbó, et al., International Journal of Quantum Chemistry, vol. 32, pps. 517–545, "LCAO–MO Similarity Measures and Taxonomy", 1987.

(List continued on next page.)

*Primary Examiner*—Marc S. Hoff
*Assistant Examiner*—Hien Vo
*Attorney, Agent, or Firm*—Oblon, Spivak, McClelland, Maier & Neustadt,P.C.

[57] ABSTRACT

A method of superposing molecular conformations of a plurality of compounds containing a plurality of characteristic groups is provided involving the steps of:

(1) dividing the plurality of characteristic groups into four types selected from hydrophobicity, hydrogen-bonding donor, hydrogen-bonding acceptor and hydrogen-bonding donor/acceptor;

(2) fixing a molecule of a first compound from the plurality of compounds having a largest molecular volume and translating, rotating or both a center of mass of each of the remaining compounds of the plurality of compounds to superpose the remaining compounds with the first compound to provide a superposed group of compounds, such that characteristic groups of the same type are overlapped;

(3) assigning a score to combinations of characteristic groups present in the superposed group of compounds;

(4) summing scores from (3) for the superposed group of compounds to provide a score value for the superposed group of compounds; and (5) repeating steps (1) to (4) until a highest score value for the superposed group of compounds is found.

1 Claim, 3 Drawing Sheets

OTHER PUBLICATIONS

C. McMartin, et al., Journal of Computer–Aided Molecular Design, vol. 9, pps. 237–250, "Flexible Matching of Test Ligands to a 3D Pharmacophore Using a Molecular Superposition Force Field: Comparison of Predicted and Experimental Conformations of Inhibitors of Three Enzymes", 1995.

C. McMartin, et al., Journal of Computer–Aided Molecular Design, vol. 11, pps. 333–344, "QXP: Powerful, Rapid Computer Algorithms for Structure–Based Drug Design", 1997.

Kazuhiko Iwase, et al., "Molecular Superposing Procedure Useful For Searching Biaoactive Conformations Of Drugs," 19th Symposium on Chemical Information and Computer Science & 24th Symposium on Structure–Activity Relationships, Nov. 12–14, 1996, pp. 257–260, 390 (English Translation).

Hiroaki Ohoka, et al., "Evaluation of Molecular Structure Similarity by Fragment Spectra Method: Use of Subspectra," 19th Symposium on Chemical Information and Computer Science & 24th Symposium on Structure–Activity Relationships, Nov. 12–14, 1996, p. 390. (English Abstract of Paper).

Kazuhiko Iwase, et al., "Molecular Superposing Procedure Useful For Searching Biaoactive Conformations Of Drugs," 19th Symposium on Chemical Information and Computer Science & 24th Symposium on Structure–Activity Relationships, Nov. 12–14, 1996, p. 390. (English Abstract of Paper).

Kazuhiko Iwase, et al.,"Determination of Bioactive Conformation of Drugs by a New Superposing Procedure," The Pharmaceutical Society of Japan 117th Annual Meeting, Mar. 5, 1997, p. 129. (English Translation).

FIG. 1a

INPUT OF THREE-DIMENSIONAL COORDINATES AND CHARACTERISTIC GROUP OF COMPOUNDS

HYDROPHOBICITY, HYDROGEN-BONDING DONOR, HYDROGEN-BONDING ACCEPTOR AND HYDROGEN-BONDING DONOR/ACCEPTOR

TRANSLATING CENTERS OF MASS OF COMPOUNDS TOWARD THE ORIGIN OF COORDINATES
MAKING CIRCUMSCRIBED RECTANGULAR BOXES OF COMPOUNDS

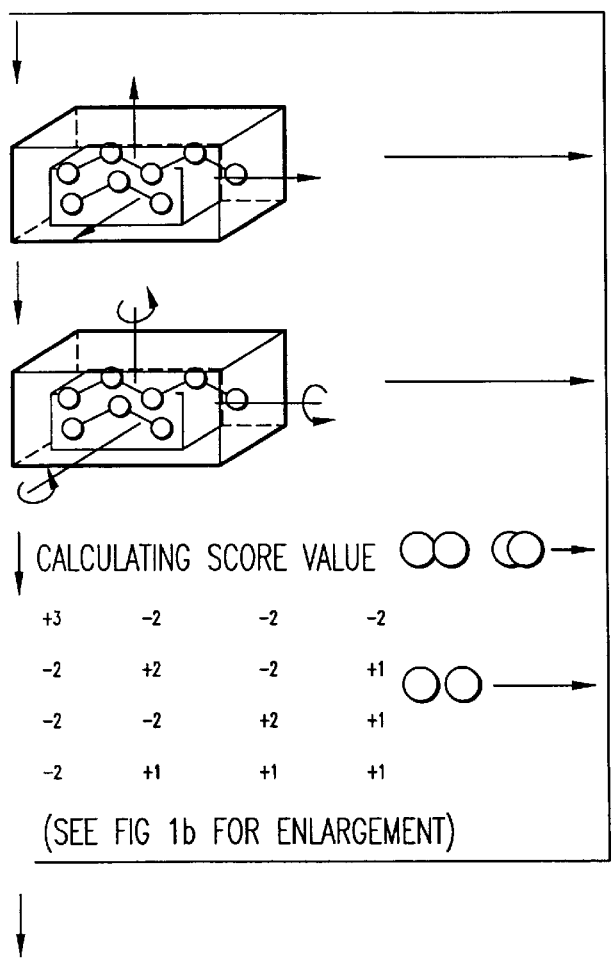

TRANSLATING OPERATION OF COMPOUND WITH SMALLER VOLUME (INCREMENT OF x, y, z-TRANSLATIONS=1Å)

SUCCESSIVE ROTATING OPERATION ($0° \leq \phi, \psi \leq 350°$, $0° \leq \theta \leq 180°$, ROTATION INCREMENT=10°)

OVERLAPPING VALID

OVERLAPPING INVALID

RADIUS OF CHARACTERISTIC SPHERE=0.5, 1.0Å

(SEE FIG 1b FOR ENLARGEMENT)

DETERMINING THE BEST ORIENTATION

EVALUATION CRITERION (ORDER OF PREFERENCE)
1) HIGHEST SCORE VALUE   2) MINIMUM STANDARD DEVIATION OF ERRORS IN DISTANCE BETWEEN CHARACTERISTIC GROUPS

OPTIMIZING ORIENTATION BY SIMPLEX METHOD
CONVERGENT CONDITION: STANDARD DEVIATION<0.01

FIG. 1b

CALCULATING SCORE VALUE

|  | HYDRO-PHOBICITY | HYDROGEN-BONDING DONOR | HYDROGEN-BONDING ACCEPTOR | HYDROGEN-BONDING DONOR/ACCEPTOR |
|---|---|---|---|---|
| HYDROPHOBICITY | +3 | −2 | −2 | −2 |
| HYDROGEN-BONDING DONOR | −2 | +2 | −2 | +1 |
| HYDROGEN-BONDING ACCEPTOR | −2 | −2 | +2 | +1 |
| HYDROGEN-BONDING DONOR/ACCEPTOR | −2 | +1 | +1 | +1 |

HIV-1 PROTEASE INHIBITORS
THICK LINE: A-74704
THIN LINE: MVT-101

THROMBIN INHIBITORS
THICK LINE: NAPAP
THIN LINE: MQPA

METHOD OF SUPERPOSING MOLECULAR CONFORMATIONS OF COMPOUNDS

BACKGROUND OF THE INVENTION

The present invention provides a novel method of superposing molecular conformations of compounds for drugs, agricultural chemicals, etc., and it can be applied in the process of determining bioactive conformation from many stable conformations.

The invention provides a novel technique of superposing molecular conformations of compounds that is utilizable for the creation of lead compounds for drugs, agricultural chemicals, etc., based on the exploration of the bioactive conformation and pharmacophore.

In computer assissted drug designs of drugs and agricultural chemicals, it is very important to determine the conformation of ligand molecule in the state of binding to proteins such as receptor and enzyme, that is, the bioactive conformation thereof. As a method of experimentally determining the bioactive conformation of this ligand molecule, X-ray crystallography of complex with proteins or NMR spectroscopy has been known. However, it is generally accompanied with many difficulties that the crystallization of proteins such as receptor and enzyme is difficult, that enough quantity for analysis cannot be obtained, that molecular weight is too large to analyze, and the like. For this reason, in computer assisted drug designs, an approach is taken to presume the bioactive conformation, based on the crystal structure of ligand molecule alone or the structure obtained from calculation by molecular mechanics or molecular orbital method in a system that does not clearly deal with the solvent molecules.

It has been considered that, even if the bioactive conformation may not be the same as the most stable conformation obtained from calculation, it comes to be a stable conformation not so away from the most stable conformation, in view of energy. Moreover, for the conformations of ligand molecules binding to the same receptor or enzyme, a common feature that there is the same characteristic group in the same site in three-dimensional space is considered, hence the superposition among characteristic groups of the stable conformations is effective for the extraction of bioactive conformation. For example, it appears to be also possible to sample many stable conformations using molecular dynamics calculation on some ligand molecules and perform the superposition among those stable conformations based on the constituting characteristic group to determine the bioactive conformation common to each ligand molecule.

For the superposition among molecules, it is common to perform so that the positions coincide with each other between the corresponding atoms. For this reason, an operation for determining beforehand the pharmacologically effective atoms of compounds is needed. However, the atomic positions are not needed to coincide for binding to proteins such as receptor and enzyme and, additionally, there are many receptors for which even the existence, to say nothing of information of three-dimensional structures thereof, is not grasped, so the problems are complicated. Hence, the results of interactive superposition tend to be influenced by the intuition and experience of analyst.

While, Y. C. Martin et al developed an automatic exploratory technique of superposition (DISCO) by improving the conventional technique of matching the distance between pharmacophore centers, wherein the allowable error was taken in for the coincidence of atomic positions and further the direction of hydrogen bond and the orientation of aromatic ring were also taken into account, and applied it to dopamine agonist and benzodiazepine agonist (Y. C. Martin et al, J. Compt.-Aided Mol. Design, 7, 83–102(1993)).

In others, techniques of evaluating the superposition from the similarity of the electron density, electrostatic potential and volume of molecule are reported by Carbo (R. Carbo, L. Leyda and M. Arnau, Int. J. Qant. Chem., 17, 1185–1189 (1980); R. Carbo and L. Domingo, Int. J. Qant. Chem., 32, 517–545(1987)) and by Hodgkin (W. G. Richards and E. E. Hodgkin, Chemistry in Britain, 1141–1144(1988); E. E. Hodgkin and W. G. Richards, Int. J. Qant. Chem., 14, 105–110(1987)), and the automatic exploration of superposition can be realized with ASP package (C. Burt, W. G. Richards and P. Huxley, J. Comput. Chem., 11, 1139–1146 (1990)).

In recent years, proceeding this further, T. D. Perkins et al developed a technique that took the similarity of volume, hydrogen bond and electrostatic potential into account and applied it to some inhibitors. Thereamong, the automatic exploration of superposition between serine protease inhibitors with different sizes attracts an attention (T. D. Perkins, J. E. J. Mills and P. M. Dean, J. Compt.-Aided Mol. Design, 9, 479–490(1995)).

However, the method of Y. C. Martin et al has restrictions that the number of functional groups constituting the pharmacophore should be equal between compounds, that the correspondence between atoms and between functional groups should be taken into account, and the like.

Also, the method of T. D. Perkins et al takes considerable calculating time on the whole, and it requires difficulty to determine the bioactive conformation using this technique.

For this reason, simpler and more rapid method of superposing the molecules of compounds has been required.

The inventors studied diligently to solve the subject aforementioned and, in the method of superposing the molecular conformations of compounds, they have found a method of performing the superposition based on the properties of characteristic group constituting that molecule of compounds, leading to the completion of the invention.

SUMMARY OF THE INVENTION

The invention provides a method of superposing the molecular conformations of compounds characterized in that, upon superposing the molecular conformations of a plurality of compounds, (1) the characteristic groups of compounds are roughly divided into four types of hydrophobicity, hydrogen-bonding donor, hydrogen-bonding acceptor and hydrogen-bonding donor/acceptor, (2) a molecule of compound with the largest volume is fixed and other molecules of compounds are operated to translate and rotate their centers of mass to perform the superposition, (3) when overlapping of characteristic groups is caused between molecules of compounds by the operation of translation and rotation in (2), a score is given depending on the combination between respective characteristic groups, and (4) scores are summed up on all the combinations of characteristic groups constituting the molecules of compound. Said operations of (1) through (4) are repeated to find out an orientation that acquires the highest score value.

According to the superposing method of the invention, it is not needed to take the correspondence of individual characteristic group between the molecules of compounds into account, an operation of determining beforehand the pharmacophore of compounds is not needed, and the atomic positions are also not needed to coincide accurately on superposing between molecules of compounds. The inventive superposing method is simple and rapid and can be applied to presume the bioactive conformation out of many stable conformations of molecules of compounds.

BRIEF DESCRIPTION OF THE DRAWING

FIG. 1 is an illustration diagram showing the process of superposition according to the invention.

DETAILED DESCRIPTION OF THE INVENTION

Figure 2:
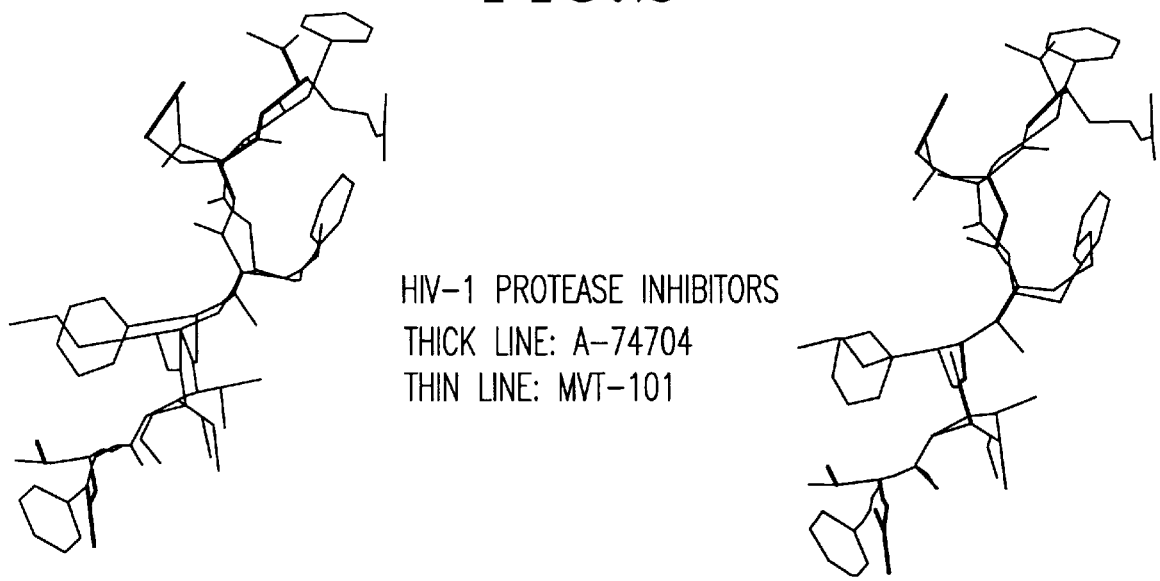
FIG. 2 is an illustration diagram showing the result of Example 1.

The process of superposition is shown in FIG. 1. In following, each step will be explained.

The properties of characteristic groups are roughly divided into four types of hydrophobicity, hydrogen-bonding donor, hydrogen-bonding acceptor and hydrogen-bonding donor/acceptor, and a score is given to every overlapping thereof. And, if characteristic groups with the same properties are overlapped between them, then the score adds points, and, if characteristic groups with different properties are overlapped between them, it is taken off points but, characteristic groups having no overlapping are not made as a target of score (Table 1). However, the redundancy of overlapping with more than one pair between characteristic groups with the same properties is not admitted. Thereafter, the scores are summed up on all the combinations of characteristic groups constituting the molecules.

TABLE 1

Score value between characteristic groups

| | Hydro-phobicity | Hydrogen-bonding donor | Hydrogen-bonding acceptor | Hydrogen-bonding donor/acceptor |
|---|---|---|---|---|
| Hydrophobicity | +3 | −2 | −2 | −2 |
| Hydrogen-bonding donor | −2 | +2 | −2 | +1 |
| Hydrogen-bonding acceptor | −2 | −2 | +2 | +1 |
| Hydrogen-bonding donor/acceptor | −2 | +1 | +1 | +1 |

Here, the absolute values of figures in table are those exemplified and not fixed.

Since the atomic positions are not needed to coincide for binding to proteins such as receptor and enzyme, each characteristic group is approximated with a sphere, and, if two spheres are overlapped even a little, they are made as a target of score. The radii of the spheres of characteristic groups are considered to be different in size between resonance system and others, and, for example, it is possible to put the resonance system on 0.5 angstroms and others on 1 angstrom.

Each characteristic group building the molecule is allotted based on, for example, following rules.

1. Oxygen atom of carbonyl, sulfon, phosphon, ester, ether, etc. is hydrogen-bonding acceptor.
    a) In the resonance conformations of $CO_2^-$, $SO_2$, $PO_2^-$, etc., the radius of hydrogen-bonding acceptor sphere is 0.5 angstroms.
    b) In a), it is also possible to place 1 angstrom hydrogen-bonding acceptor sphere in the middle of two oxygen atoms.

2. Oxygen atom of hydroxyl group and sulfur atom of thiol are hydrogen-bonding donor/acceptor.

3. Nitrogen atom accompanying with hydrogen atom such as amine, amide, amidine or guanidine is hydrogen-bonding donor.
    a) In the resonance conformations of amidine etc., the radius of hydrogen-bonding donor sphere is 0.5 angstroms.
    b) In a), it is also possible to place 1 angstrom hydrogen-bonding donor sphere in the middle of two nitrogen atoms.

4. Aromatic ring of phenyl, naphthalene, pyridine, thiophene, etc. is hydrophobic.
    a) 0.5 Angstroms hydrophobic spheres are placed at the root of aromatic ring and at positions each leaving one space in the clockwise and counterclockwise directions.
    b) In a), it is also possible to place 1 angstrom hydrophobic sphere at the center of ring.

5. Aliphatic chain (including branched chain) with alkyl (including thioether) chain length of three or more as a characteristic group is hydrophobic.
    a) 1 Angstrom hydrophobic sphere is placed on carbon atom at branched position.
    b) 1 Angstrom hydrophobic sphere is placed on carbon atom at the third position counting from the position of the root of main chain (the atom at the root should not be allotted already as a characteristic group, otherwise counting is made from next atom).
    c) It is impossible to place the hydrophobic sphere, unless separating two or more carbon atoms from the characteristic group having polarity.
    d) It is impossible to continuously place the hydrophobic spheres (two atoms should be interposed).
    e) It is possible to place 1 angstrom hydrophobic sphere at the center of ring for piperidine ring and pyrrolidine ring.

6. Trifluoromethyl group is hydrophobic and 1 angstrom hydrophobic sphere is placed on central carbon atom.

For systematically performing the superposition of two molecules, first, the center of mass of each molecule is translated toward the origin of coordinates and then the curcumscribed rectangular boxes are calculated. And, fixing the molecule with larger volume, the molecule with smaller volume is translated and rotated. This translation and rotation are always performed in terms of the center of mass of translating molecule. The range of translation is a maximum distance that the center of mass can translate, for example, when placing the circumscribed rectangular box with smaller volume in the circumscribed rectangular box with larger volume. The translational increment is 1 angstrom and translation is assumed to be made on the body-centered cubic lattice points made in the circumscribed rectangular box with larger volume.

The rotation is performed on each of said lattice points and the ranges were made to be $0 \leq \phi, \psi \leq 350°$ and $0 \leq \theta \leq 180°$ using three Eulerian angles; the rotational increment was made to be 10°.

Score is calculated on the orientations of all of said superpositions, respectively, and an orientation with the highest value is adopted. If the highest value of score is redundant, then one with smaller standard deviation of errors in the distance between characteristic groups is selected conveniently. To take care, however, it may be required to examine also on some orientations with the same score. For further improving the score of orientation adopted, translational vectors and three Eulerian angles are optimized by simplex method using the standard deviation of errors as an objective function to determine the final orientation of superposition. However, for the calculation of the standard deviation of errors, the redundancy of overlapping with more than one pair between characteristic groups with the same properties is also taken into account.

EXAMPLE

The superposition of enzyme inhibitors was performed to compare with the superposition obtained from the X-ray crystallography of enzyme-inhibitor complex.

The superposition of enzyme inhibitors was performed using three-dimensional coordinates obtained from protein data bank (PDB, Brookhaven Protein Data Bank). The abbreviated name of inhibitors and the registration number of three-dimensional coordinates of enzyme-inhibitor complex (in bracket) were described using those of PDB registration.

Besides, the superposition obtained from X-ray crystallography means a superposition obtained by taking out only the coordinates of inhibitor molecules, after fitting least-squarely between α-carbon atomic of coordinates of enzyme molecules in enzyme-inhibitor complex.

Example 1

HIV-1 protease inhibitors
A-74704 (9HVP) & MVT-101 (4HVP)

Example 2

Thrombin inhibitors
NAPAP (1ETS) & MQPA (1ETR)

Example 3

Thrombin inhibitors
MQPA (1ETR) & 4-TAPAP (1ETT)

Example 4

Trypsin inhibitors
PRA (1TNK) & AMC (1TNG)

Example 5

Trypsin inhibitors
PRA (1TNK) & BEN (2TBS)

Example 6

Carboxypeptidase A inhibitors
FVF (7CPA) & BZS (1CBX)

Example 7

Carboxypeptidase A inhibitors
FVF (7CPA) & AGF (8CPA)

Example 8

Elastase inhibitors
BDK (1EAU) & TFK (1EAS)

Example 9

Elastase inhibitors
TFA-Lys-Ala-ANI (2EST) & TFA-Leu-Ala-ANI (7EST)

Example 10

Elastase inhibitors
TFK (1EAS) & TFA-Lys-Leu-ISO (1ELB)

Example 11

Elastase inhibitors
Part of OMTKY3 (1PPF) &
ACE-Ala-Pro-Val-FPA (4EST)

Example 12

Thermolysin inhibitors
CBZ-PGL-Leu-Leu (5TMN) &
PHO-Leu-NH2 (2TMN)

Figure 3:
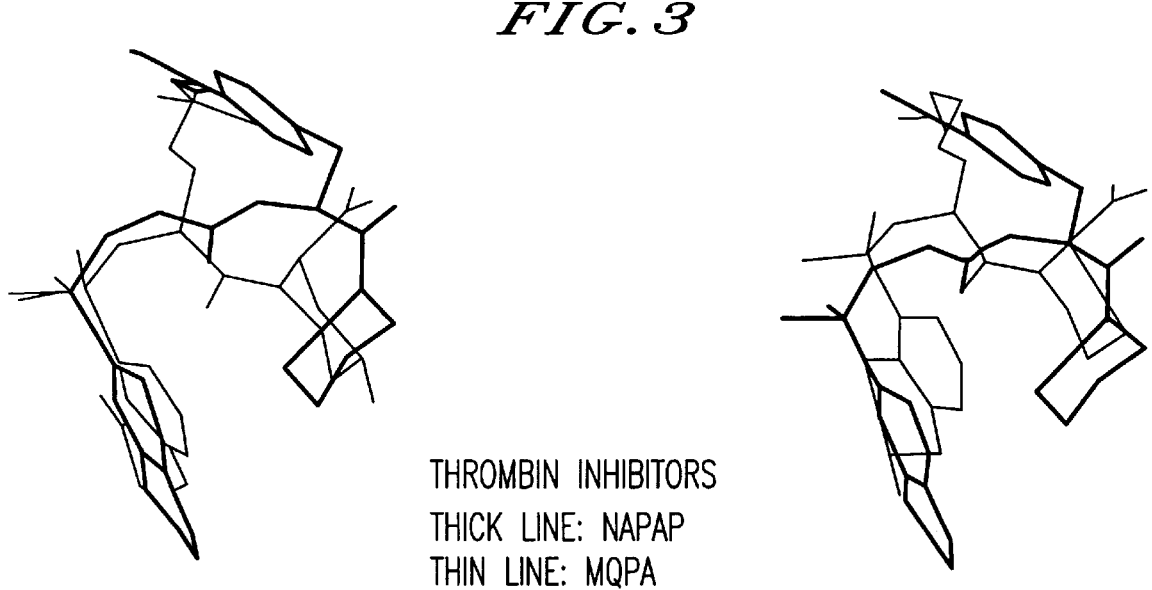
FIG. 3 is an illustration diagram showing the result of Example 2.

The results of Examples 1 and 2 are shown in FIG. 2 and FIG. 3. In the diagrams, left side is the superposition obtained by the invention and right side is that obtained by X-ray crystallography.

All the superpositions between enzyme inhibitors in the examples reproduced the superpositions from X-ray crystallography.

What is claimed is:

1. A method of superposing molecular conformations of a plurality of compounds containing a plurality of characteristic groups, comprising:

(1) dividing said plurality of characteristic groups into four types selected from hydrophobicity, hydrogen-bonding donor, hydrogen-bonding acceptor and hydrogen-bonding donor/acceptor;

(2) fixing a molecule of a first compound from said plurality of compounds having a largest molecular volume and translating, rotating or both a center of mass of each of the remaining compounds of said plurality of compounds to superpose the remaining compounds with said first compound to provide a superposed group of compounds, such that characteristic groups of the same type are overlapped;

(3) assigning a score to combinations of characteristic groups present in said superposed group of compounds;

(4) summing scores from (3) for said superposed group of compounds to provide a score value for said superposed group of compounds; and (5) repeating steps (1) to (4) until a highest score value for said superposed group of compounds is found.

* * * * *